United States Patent [19]

Jordan et al.

[11] Patent Number: 4,814,181
[45] Date of Patent: Mar. 21, 1989

[54] DOSAGE FORM COMPRISING FAST AGENT DELIVERY FOLLOWED BY SLOW AGENT DELIVERY

[75] Inventors: Maureen L. Jordan, Mt. View; Atul D. Ayer; Paul R. Magruder, both of Palo Alto; David E. Edgren, El Granada, all of Calif.

[73] Assignee: ALZA Corporation, Palo Alto, Calif.

[21] Appl. No.: 92,857

[22] Filed: Sep. 3, 1987

[51] Int. Cl.⁴ ............................................. A61K 9/24
[52] U.S. Cl. .................................. 424/473; 424/467; 424/472
[58] Field of Search ................................ 424/473, 467

[56] References Cited

U.S. PATENT DOCUMENTS

| | | | |
|---|---|---|---|
| 4,320,759 | 3/1982 | Theeuwes | 424/473 |
| 4,449,983 | 5/1984 | Cortese et al. | 424/473 |
| 4,475,916 | 10/1984 | Himmelstein | 424/473 |
| 4,643,731 | 2/1987 | Eckenhoff | 424/473 |
| 4,673,405 | 6/1987 | Guittard et al. | 424/473 |

Primary Examiner—William R. Dixon, Jr.
Assistant Examiner—David M. Brunsman
Attorney, Agent, or Firm—Paul L. Sabatine; Edward L. Mandell; Steven F. Stone

[57] ABSTRACT

A dosage form is disclosed comprising a wall that surrounds a compartment with an exit means in the wall. The compartment comprises a first or fast releasing lamina and a second or short releasing lamina that are delivered through the exit means over two different periods of time.

20 Claims, 3 Drawing Sheets

DOSAGE FORM COMPRISING FAST AGENT DELIVERY FOLLOWED BY SLOW AGENT DELIVERY

CROSS REFERENCED TO CO-PENDING APPLICATION(S)

This application is co-pending with U.S. patent application Ser. No. 07/034,971 filed Apr. 6, 1987, further identified as attorney docket number ARC 1397. Both this application and the copending application are assigned to ALZA Corporation of Palo Alto, Calif.

FIELD OF THE INVENTION

This invention pertains to both a novel and useful dosage form for delivering a beneficial agent to an environment of use. More particularly, the invention relates to a dosage form comprising a wall that surrounds a compartment. The compartment comprises a first lamina comprising a beneficial agent that is delivered in a short period of time, and a second lamina comprising a beneficial agent that is delivered in a prolonged period of time. At least one passageway through the wall permits delivery of the first lamina comprising its beneficial agent and delivery of the second lamina comprising its beneficial agent to an environment of use.

BACKGROUND OF THE INVENTION

Since the beginning of antiquity those engaged in pharmacy and medicine have sought a dosage form designed as a delivery system for the controlled administration of a beneficial agent to an environment of use. The first written reference to a delivery system, a dosage form, is in the Eber Papyrus written about 1552 B. C. The Eber Papyrus mentions dosage forms such as anal suppositories, vaginal pessaries, ointments, oral pill formulations and other dosage r preparations. About 2500 years passed without any advance in dosage form development until the Arab physician Rhazes, 865-925 A. D., invented the coated pill. About a century later the Persian Avicenna, 980-1037 A. D., coated pills with gold or silver for increasing patient acceptability and for enhancing the effectiveness of the drug. Also around this time the first tablet was described in Arabian manuscripts written by Al-Zahrawi, 936-1009 A. D. The manuscripts described a tablet formed from the hollow impressions in two matched, facing tablet molds. Pharmacy and medicine waited about 800 years for the next innovation in dosage forms when in 1883 Mothes invented the capsule for administering a drug. The next quantum and profound leap in dosage forms came in 1972 with the invention of the osmotic delivery device invented by Theeuwes and Higuchi. This unique osmotic delivery device is manufactured in one embodiment for oral use. In this embodiment, it embraces the appearance of a tables comprising an internal drug core and a delivery portal. After a start-up period, it delivers drug at a controlled rate over a prolonged period of time. It is the first oral dosage form that delivers a drug throughout the entire gastrointestinal tract in a controlled dose per unit time.

While the above described osmotic system comprising a single drug core represents an outstanding and pioneering advancement in the osmotic delivery art, and while the osmotic system is useful for dispensing innumerable drugs to the environment of use, it has now been discovered that these osmotic systems can be improved further to enhance the delivery kinetics and the usefulness of the osmotic systems. That is, it now has been unexpectedly discovered that a novel dosage form manufactured as an osmotic device can be provided to deliver a bio-affecting drug at a fast rate and deliver a bio-affecting drug at a slow rate in a substantially constant dose over a prolonged period of time. By providing a fast rate of delivery the dosage form makes drug available early in the delivery period and essentially eliminates the start-up time associated with the prior art osmotic dosage forms. The dosage form by providing a slow rate of delivery also makes available drug delivery at a controlled and constant rate over a prolonged period of time. The dosage form made available by this invention uniquely embodies delivery at two different rates, thereby functioning according to a pre-selected, built-in optimal program of drug presentation.

OBJECTS OF THE INVENTION

Accordingly, in view of the above presentation it is an immediate object of this invention to provide an improved dosage form, manufactured as an osmotic delivery device, for the controlled delivery of a drug at a fast rate and at a slow and constant, prolonged rate to a drug receptor for producing a therapeutic effect.

Another object of the invention is to provide an osmotic dosage form that comprises means for delivering a beneficial agent instantly, thereby overcoming the start-up time known to the prior art.

Another object of the invention is to provide an osmotic dosage form that comprises means for instantly delivering a beneficial agent followed by delivering a beneficial agent over a prolonged period of time.

Another object of the invention is to provide an osmotic dosage form comprising means for the concurrent and instant delivery of a beneficial agent and for delivery of a beneficial agent at a slow rate over a prolonged period of time.

Another object of the invention is to provide an osmotic dosage form comprising a wall that surrounds a compartment which compartment comprises means for providing a beneficial drug at a fast delivery rate and means for delivering a beneficial drug at a slow rate over time.

Another object of the invention is to provide an osmotic dosage form comprising a wall that surrounds a compartment, which compartment contains a drug that is available for immediate delivery for substantially eliminating the start-up time associated previously with osmotic dosage forms.

Another object of the invention is to provide an osmotic dosage form comprising a first lamina comprising a drug and a releasable binder, which lamina delivers drug immediately for increasing the period of time drug is available for performing its beneficial effects.

Another object of the invention is to provide an osmotic dosage form comprising a first delivery lamina that contains a drug and a releasable binder that delivers drug immediately, and a slow delivery second lamina that contains a drug and preferably a different releasable binder that delivers the drug at a slower rate over a prolonged period of time.

Another object of the present invention is to provide a dosage form comprising a beneficial drug that can be from insoluble to very soluble in an aqueous fluid, and which drug can be delivered by the dosage form at two different rates of drug delivery.

Another object of this invention is to provide a dosage form that can administer to a warm-blooded host a complete pharmaceutical regimen comprising poorly soluble drugs to very soluble drugs that are made available immediately and also at a controlled and continuous rate for a prolonged particular time period, the use of which requires intervention only for initiation and possible termination of the therapeutic regimen.

Another object of the present invention is to provide a dosage form for delivering a drug in the gastrointestinal tract that substantially avoids a premature break-up and undergoes a change in its drug delivery rate from a fast to a slower rate of drug delivery over a prolonged period of time of at least eight hours.

Another object of the invention is to provide a laminae comprising a fast drug releasing lamina in laminar arrangement with a slow drug releasing lamina which laminae comprise a water soluble composition for releasing a drug in the laminae in the presence of water or in a biological fluid that enters the laminae.

Another object of the invention is to provide an oral, osmotic device that dispenses a drug at a fast rate followed by release of drug at a slow rate, which rates in either instance are controlled by the osmotic device.

Other objects, features and advantages of the invention will be more apparent to those skilled in the dispensing art from the following detailed specification, taken in conjunction with the drawing figures and the accompanying claims.

BRIEF DESCRIPTION OF THE DRAWINGS

In the drawing figures, which are not drawn to scale, but are set forth to illustrate various embodiments of the invention, the drawing figures are as follows.

DETAILED DESCRIPTION OF THE DRAWINGS

Figure 1:
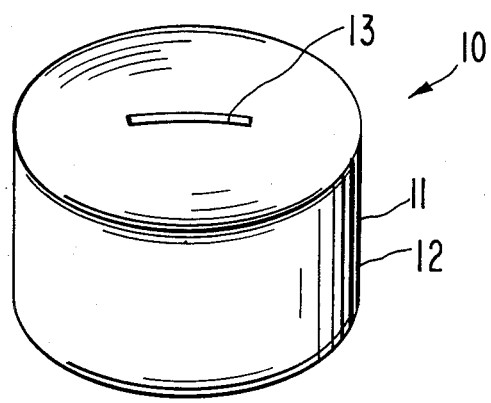
FIG. 1 is a side, elevated view of a dosage form provided by this invention designed and shaped for oral administration to the gastrointestinal tract of an animal, the dosage form comprising two distinct lamina comprising a beneficial drug in each lamina.

Turning now to the drawing figures in detail, which drawing Figures are an example of the dosage forms provided by this invention, and which examples are not to be construed as limiting, one example of this dosage form is illustrated in FIG. 1 designated by the numeral 10. In FIG. 1, dosage form 10 is manufactured as an oral device comprising a body 11. Dosage form 10 comprising body 11 can be shaped, sized, adapted and structured for easy placement and prolonged retention in a biological environment of use for the controlled delivery of a beneficial agent thereto. Dosage form 10 comprises wall 12 with a passageway 13 for connecting the inside of the dosage form 10 with the exterior of the dosage form.

Figure 2:
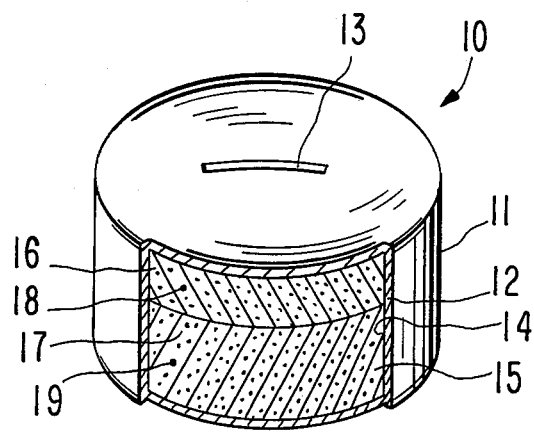
FIG. 2 is an opened view of the dosage form of FIG. 1 for illustrating the internal structure of the dosage form.

In FIG. 2, dosage form 10 is seen in opened section. In FIG. 2, dosage form 10 comprises body 11 having a wall 12. Wall 12 surrounds and forms an internal compartment. Wall 12 is opened at 14 for illustrating internal compartment 15. Wall 12 comprises in at least a part a semipermeable composition that is permeable to the passage of an exterior fluid present in the environment of use, and it is substantially impermeable to the passage of a beneficial agent and other ingredients that may be present in compartment 15. Wall 12 of dosage form 10 is substantially inert, that is it maintains its physical and chemical integrity during the dispensing of a beneficial agent, and it is formed of a non-toxic composition. Dosage form 10, as seen in FIG. 1 and FIG. 2, can be made of any conventional geometric shape such as an ellipsoid, or bean shaped, circular shaped, rectangular shaped, caplet shaped and the like.

In FIG. 2, dosage form 10 comprises in compartment 15 a first lamina 16 and a second lamina 17. First lamina 16 and second lamina 17 are in contacting arrangement and they function in concert for providing a complete beneficial delivery program. First lamina 16 comprises a beneficial agent 18, preferably a beneficial drug, and second lamina 17 comprises a beneficial agent 19, such as a drug.

First lamina 16 comprising beneficial agent 18 is a fast releasing lamina. The phrase, "fast releasing lamina", as used for the purpose of this invention, generically denotes that when dosage form 10 is in operation in the environment of use fast releasing lamina 16 is released from dosage form 10 during the first hours of operation. Fast releasing lamina 16 is dispensed by, for example, going into solution or forming a dispensable semi-viscous carrier almost immediately and it delivers beneficial agent 18 almost immediately to a fluid biological environment of use. The release of fast dissolving lamina 16 with beneficial agent 18 overcomes a delayed start-up time in agent delivery, thereby when beneficial agent 18 is a drug, it is made available to produce early plasma concentrations of drug in a therapeutic program in a warm-blooded animal, including humans.

In a presently preferred embodiment fast releasing lamina 16 comprises a hydroxypropylcellulose and other lamina 16 forming components such as hydroxypropylmethylcellulose, polyvinyl pyrrolidone, an effervescent agent such as sodium bicarbonate, potassium bicarbonate, and the like, a buffer such as sodium acetate, potassium acetate and the like, a beneficial agent, and the like. The hydroxypropylcellulose used for the purpose of this invention is a nonionic ether with a neutral pH range and a hydroxypropyl content of 7% to 16%. More specific hydroxypropylcelluloses comprising a hydroxypropyl content of 7% to 10%, a hydroxypropyl content of 10% to 13%, and a hydroxypropyl content of 13% to 16%. In the embodiments wherein lamina 16 comprises a hydroxypropylmethylcellulose, the hydroxypropylmethylcellulose preferably comprises a hydroxypropyl content of 4% to 12% and a methyloxy content of 19% to 24%. Exemplary hyroxypropylmethylcelluloses that can be used for forming lamina 16 comprises a member selected from the group consisting of (a) a hydroxypropylmethylcellulose having a degree of polymerization (DP) of about 50, a viscosity of about 3 centipoises measured as a 2% solution in water, and a number average molecular weight of about 9,200; (b) a hydroxypropylmethylcellulose exhibiting a viscosity of about 3 centipoises, a degree of polymerization of about 51, and a number average molecular weight of about 9,600; (c) a hydroxypropylmethylcellulose having a viscosity of 5, a degree of polymerization of 56, and a number average molecular weight of 11,300; (d) a hydroxypropylmethylcellulose having a viscosity of 15, a degree of polymerization of 79 and a number average molecular weight of 15,900; and (e) a hydroxypropylmethylcellulose having a viscosity of 35, a degree of polymerization of 102 and a number average molecular weight of 19,600. Generally a hydroxypropylmethylcellulose used for forming fast releasing lamina 16 will comprise a number average molecular weight of about 9,000 to 25,000. Fast releasing lamina 16 generally comprises about 5% to 50% of hydroxypropylcellulose, and 2% to 15% of hydroxypropylmethylcellulose. Fast releasing lamina 16 in another preferred embodiment can comprise a binder such as polyvinylpyrrolidone, lightly cross-linked polyvinylpyrrolidone, and the like.

The expression, "slow releasing lamina 17" as used herein denotes lamina 17 is released through passageway 13 at a controlled and continuous rate of 1½ hours to 14 hours or longer. The period of time in some preferred embodiments generally is from 2 hours to 12 hours. Slow releasing lamina 17 comprising beneficial agent 19 releases beneficial agent 19 over a corresponding period of time to the environment of use.

Lamina 17 in a presently preferred manufacture comprises a hydrogel, a cellulosic polymer and a beneficial agent. Representative hydrogel comprise a polyalkylene oxide. The polyalkylene oxide can include a homopolymer of ethylene oxide, propylene oxide and butylene oxide, and copolymers of ethylene oxide, propylene oxide and butylene oxide. The polyalkylene oxides used herein generally have an average molecular weight of about 10,000 to 5,000,000 and in a presently preferred embodiment an average molecular weight of 10,000 to 900,000. The degree of polymerization is about 200 to 115,000. The presently preferred polyalkylene oxide is polyethylene oxide exhibiting a number average molecular weight of 10,000 to 200,000. Polyalkylene oxides are known to the art in U.S. Pat. No. 3,963,805 and 4,211,681.

In a presently preferred embodiment the cellulosic polymer used for manufacturing lamina 17 comprise a hydroxypropylmethylcellulose having a number average molecular weight of from 9,000 to 250,000. The hydroxypropylmethylcellulose present in slow releasing lamina 17 can be the same or different than the hydroxypropylmethylcellulose present in fast releasing lamina 16. In a presently preferred proviso lamina 17 differs from lamina 16 wherein lamina 16 comprises hydroxy- propylcellulose.

Representative hydroxypropylmethylcellulose polymers useful for the manufacture of slow releasing lamina 17 comprises (a) hydroxypropylmethylcellulose exhibiting a viscosity of 3, a degree of polymerization of 48 and a number average molecular weight of 9,200; (b) a hydroxypropylmethylcellulose exhibiting a viscosity of 35, a degree of polymerization of 102 and a number average molecular weight of 19,600; (c) a hydroxypropylmethylcellulose having a viscosity of 100, a degree of polymerization of 145 and a number average molecular weight of 27,800; (d) a hydroxypropylmethylcellulose having a viscosity of 4,000, a degree of polymerization of 460 and a number average molecular weight of 88,300; (e) a hydroxypropylmethylcellulose having a viscosity of 15,000, a degree of polymerization of 690 and a number average molecular weight of 132,500; (f) a hydroxypropylmethylcellulose exhibiting a viscosity of 100,000, a degree of polymerization of 1,260 and a number average moleular weight of 241,900 and the like. Lamina 17 in another embodiment comprises the cellulose polymer carboxymethylcellulose, such as sodium carboxymethylcellulose.

Wall 12 of dosage form 10 comprises neat, or at least in part, a semipermeable wall forming composition that does not adversely affect the beneficial agent, an animal host and other components comprising dosage form 10. Wall 12 is permeable to the passage of an external fluid present in the environment of use such as water and biological fluids, and wall 12 is substantially impermeable to the passage of beneficial agents and other components comprising dosage form 10. The selectively semipermeable materials useful for manufacturing wall 12 are, in a presently preferred embodiment, non-erodible and they are insoluble in fluids. Typical polymeric materials for forming wall 12 comprise a member selected from the group consisting of cellulose esters, cellulose ethers and cellulose ester-ethers. The cellulosic polymers have a degree of substitution, D.S., on their anhydroglucose unit from greater than 0 up to 3, inclusive. By degree of substitution is meant the average number of hydroxyl groups originally present on the anhydroglucose unit comprising the cellulose polymer that are replaced by a substituting group. Representative polymeric materials include a member selected from the group consisting of cellulose acylate, cellulose diacylate, cellulose triacylate, cellulose acetate, cellulose diacetate, cellulose triacetate, mono-, di- and tri-cellulose alkanylates, mono-, di- and tri-cellulose aroylates, and the like. Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21% to 35%; cellulose triacetate having a D.S. of 2 to 3 and an acetyl content of 35% to 44.85; and the like. Examples of more specific cellulose polymers include cellulose propionate having a D.S. of 1.8 and a propionyl content of 39.2% to 45% and a hydroxyl content of 2.8% to 5.4%; cellulose acetate-butyrate having a D.S. of 1.8 and an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate, and the like. Additional semipermeable polymers that can be used for manufacturing wall 12 include acetaldehyde dimethyl acetate, cellulose acetate ethylcarbamate, cellulose acetate phthalate for use in environments having a low pH, cellulose acetate methyl carbamate, cellulose acetate dimethylaminoacetate, semipermeable polyamides, semipermeable polyurethanes, semipermeable sulfonated polystyrenes, cross-linked selective semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; lightly cross-linked plasticized polystyrene derivatives; cross-linked poly(sodium styrene sulfonate); crosslinked poly(vinylbenzyltrimethyl ammonium chloride); semipermeable polymers exhibiting a fluid permeability of $10^{-5}$ to $10^{-1}$ (cc.mil/cm$^2$hr.atm) expressed as per atmosphere of hydrostatic or osmotic pressure difference across the semipermeable wall. The polymers are known to the art in U.S. Pat. Nos. 3,845,770; 3,916,889; and 4,160,020; and in *Handbook of Common Polymers* by Scott, J. R. and Roff, W. J., (1971) published by CRC Press, Cleveland, Ohio.

Dosage form 10 comprises a beneficial agent 18 in fast releasing lamina 16 and a beneficial agent 19 in slow releasing lamina 17. The beneficial agent can be the same in both lamina, or the beneficial agent can be different in both lamina. The expression, "beneficial agent", as used herein, in a preferred embodiment, denotes a drug. In the present specification and claims the term, "drug" includes any physiologically or pharmacologically active substance that produces a local or systemic effect in animals, including warm-blooded mammals, humans and primates; avians; household, sport and farm animals; laboratory animals; fishes; reptiles; and zoo animals. The term, "physiologically", as used herein, denotes the administration of a drug to produce generally normal levels and functions in a warm-blooded animal. The term, "pharmacologically" generally denotes variations in response to the amount of drug administered to the host. See *Stedman's Medical Dictionary*, (1966) published by Williams and Wilkins, Baltimore, Md.

The beneficial drug that can be delivered by the dosage form includes inorganic and organic compounds without limitation, including drugs that act on the peripheral nerve, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, organ systems, reproductive system, skeletal system, autocoid systems, alimentary and excretory systems, inhibitors of autocoids, and histamine systems. The therapeutic drug that can be delivered for acting on these recipients include anticonvulsants, analgesics, anti-Parkinsons, anti-inflammatories, anesthetics, antimicrobials, antimalarials, antiparasitic, antihypertensives, angiotensin converting enzyme inhibitor, antihistamines, antipyretics, alpha-adrenergic agnoist, alpha-blockers, biocides, bactericides, bronchial dilators, beta-adrenergic stimulators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, calcium channel blockers, and the like.

Exemplary drugs that can be delivered by fast drug releasing lamina 16, and by slow drug releasing lamina 17 of dosage form 10 are drugs that are very soluble in aqueous fluids such as prochlorperazine edisylate, ferrous sulfate, aminocaproic acid, potassium chloride, mecamylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodine, tridihexethyl chloride, phenformin hydrochloride, methylphenidate hydrochloride, cimetidine hydrochloride theophylline cholinate, cephalexin hydrochloride, and the like.

Exemplary drugs that can be delivered by fast drug releasing lamina 16 and by slow drug releasing lamina 17 of dosage form 10 are drugs that are poorly soluble in aqueous fluids such as diphenidol, meclizine hydrochloride, prochlorperazinemaleate, phenoxybenzamine, thiethylperazine maleate, anisindone, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esterogenic, progestational, corticosteroids, hydrocortisone, hydrocorticosterone acetate, cortisone acetate, triamcinolone, methyltesterone, 17-beta-estradiol, ethinyl estradiol, prazosin hydrochloride, ethinyl estradiol 3-methyl ether, pednisolone, 17-alpha-hydrocyprogesterone acetae, 19-norprogesterone, norgestrel, norethindrone, progesterone, norgesterone, norethynodrel, and the like.

Examples of other drugs that can be delivered by lamina 16 and lamina 17 of dosage form 10 include aspirin, indomethacin, naproxen, fenoprofen, sulindac, indoprofen, nitroglycerin, propranolol, timolol, atenolol, alprenolol, cimetidine, clonidine, imipramine, levodopa, chloropromazine, methyldopa, dihydroxyphenylalnine, pivaloyloxyethyl ester of alpha-methyldopa, theophylline, calcium gluconate, ketoprofen, ibuprofen, cephalexin, erythromycin, haloperidol, zomepirac, ferrous lactate, vincamine, diazepam, captopril, phenoxybenzamine, nifedipine, diltiazem, verapamil, milrinone, madol, quanbenz, hydrochlorothiazide, and the like. The beneficial drugs are known to the art in *Pharmaceutical Sciences*, 14th Ed., edited by Remington, (1979) published by Mack Publishing Co., Easton, PA; *The Drug, The Nurse, The Patient, Including Current Drug Handbook*, by Falconer et al., (1974–1976) published by Sunder Co., Philadelphia, Pa.; *Medicinal Chemistry*, 3rd Ed., Vol. 1 and 2, by Burger, published by Wiley-Interscience, New York and in *Physicians' Desk Reference*, 38th Ed., (1984) published by Medical Economics Co., Oradell, N.J.

The drug in dosage form 10 in lamina 16 and in lamina 17 can be in various forms, such as uncharged molecules, molecular complexes, pharmacologically acceptable salts such as hydrochloride, hydrobromide sulfate, laurate, palmitate, phosphate, nitrite, borate, acetate, maleate, tartrate, oleate, and salicylate. For acidic drugs, salts of metals, amines or organic cations; for example, quaternary ammonium can be used. Derivatives of drugs such as ester, ethers and amides can be used. Also, a drug that is water insoluble can be used in a form that is a water soluble derivative thereof to serve as a solute, and on its release from the device is converted by enzymes, hydrolyzed by body pH or other metabolic processes to the original biologically active form.

The solubility of a beneficial agent including a drug can be determined by known techniques. One method for ascertaining the solubility of an agent consists of preparing a saturated solution comprising the fluid plus the agent as ascertained by analyzing the amount of agent present in a definite quantity of the fluid. A simple apparatus for this purpose consists of a test tube of medium size fastened upright in a water bath maintained at a constant temperature and pressure, in which the fluid and agent are placed and stirred by a rotating glass spiral. After a given period of stirring, a weight of the fluid is analyzed and the stirring continued an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed; if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin*, No. 67 of the Hygenic Laboratory; *Encyclopedia of Science and Technology*, Vol. 12, pp 542-556, (1971) published by McGraw-Hill, Inc.; and *Encyclopedia Dictionary of Physics*, Vol. 6, pp 547-557, (1962) published by Pergamon Press, Inc.

A drug can be present in lamina 16 and in lamina 17 neat or, in a preferred optional embodiment, with a binder, wetting agent, lubricant, dye or other lamina forming components. Representative binders include polyvinyl pyrrolidone, lightly cross-linked polyvinyl pyrrolidone, and the like; lubricants such as magnesium stearate and the like; wetting agents such as fatty amines, fatty quaternary ammonium salts, esters of sorbitol, and the like.

The phrase, "drug formulation" indicates the drug is present in lamina 16 and in lamina 17 neat, or accompanied by a binder, and the like. Lamina 16 and lamina 17 comprise a dosage unit amount of drug for performing a therapeutic program, that is, for producing a therapeutic effect. The amount of drug in lamina 16 or in lamina 17 generally is from about 0.05 ng to 5 g or more, with individual lamina comprising, for example, 25 ng, 1 mg, 5 mg, 10 mg, 25 mg, 100 mg, 125 mg 250 mg, 750 mg, 1.0 g, 1.2 g, 1.5 g, and the like. In a presently preferred embodiment slow releasing lamina 17 comprises more drug than does fast releasing lamina 16. Generally the amount of drug in lamina 16 to lamina 17 will be in the ratio of 1:1 to 1:15. The dosage form can be administered once, twice or three times daily.

The expression, "passageway 13" as used herein denotes an exit means in wall 12 that connects the exterior of dosage form 10 with the inside compartment 15. Exit passageway 13 is a means for releasing fast lamina 16 and slow lamina 17 to the environment of use. Dosage form 10 in one manufacture comprises a single exit passageway. In this manufacture fast lamina 16 is dispensed from the dosage form followed by slow lamina 17 through the same passageway from the dosage form. In another manufacture, dosgae form 10 comprises two passageway, one facing fast lamina 16 and another facing slow lamina 17. In this manufacture, lamina 16 and lamina 17 are dispensed through their respective passageways. Exit means 13 dispenses fast releasing lamina 16 in a period of time from greater than 1 minute to 2 hours. Exit passageway 13 is shaped and sized for delivering lamina 16 in a short period of time. Exit passageway 13 can embrace any quick-releasing shape, such as quadrilateral, rectangular, parallelogram, square, pentagonal, hexagonal, and like shape. In one embodiment exit passageway 13 can comprise a slit of from 0.25 cm to 2.0 cm in length and from 0.20 cm to 1.25 cm in width, and the like. Exit means 13 can be made by mechanical drilling, laser drilling, cutting the wall, and the like. The dimensions of exit passageway 13 for releasing the fast lamina 16 in a given time period can be ascertained by manufacturing dosgae form 10 according to the mode and manner of the invention and measuring the release thereof over time by conventional assay techniques. The slow release of lamina 17 is effected by regulating the mass per unit volume of lamina 17, for example, by using hydrogels of increasing molecular weights. Procedures for determining release rates are taught in *Pharmaceutical Sciences*, by Remington, (1970) Part V, Chapter 36, "Testing and Analysis"; Chapter 37, "Analysis of Medicinals"; Chapter 38, "Biological Testing"; Chapter 39, "Clinical Analysis"; Chapter 40, "Chromatograph" and Chapter 41, "Instrumental Methods of Analysis"; published by Mack Publishing Company, Easton Pa.

Dosage form 10, in one presently preferred manufacture, is manufactured by first making independently lamina 16, or lamina 17, which laminae are made from a well mixed composition of laminae forming members For example, a particular lamina is made as follows: first, each of the ingredients comprising a lamina are independently screened and then blended together, except for the lubricant. Then the homogeneous blend is wet granulated by adding a solvent such as anhydrous ethanol, and the wet ingredients mixed until a uniform blend is obtained by said process. Next, the wet blend is passed through a screen and dried to evaporate the solvent. The resulting granules are passed again through a sieve. Next, a small amount of a finely divided lubricant is added to the dry granules and the lubricant and granules blended to provide a uniform blend. Next, the above described procedure is repeated for the other lamina.

Next, the two lamina forming compositions are fed independently into separate hoppers of a compression machine. The machine lightly compresses one lamina and then adds the second lamina forming granulation in laminating arrangement to the first lamina and then compresses the two laminae together. Typically, about two tons of pressure are applied to laminate the laminae and yield the final dosage form.

In another manufacture the dosage form 10 can be made by a dry granulation process of manufacture. The dry process comprises first mixing, for a particular lamina, all the lamina forming ingredients, except for the lubricant, passing the mixed ingredients through a grinding mill to a small mesh size, and then transferring the sized powder to a dry compactor. The compactor densifies the powder, which dense powder is then passed through a sizing mill to regrind the composition. The composition is ground to a small size, typically 20 mesh or smaller Finally, a dry lubricant is added and the ingredients blended to produce the final lamina forming composition. The second lamina is made in a similar manner. Then, each composition is fed independently to the compaction press and compressed into the dosage form comprising parallel laminae.

Other standard manufacturing procedures can be used to form the laminae and the laminated dosage form. For example, the various ingredients can be mixed with a solvent by ballmilling, calendering, stirring or rollmilling, and then pressed into a preselected sized and shaped lamina A second lamina made in a like process comprising a shape and size corresponding to the first lamina is then laminated with pressure to the first lamina to yield this structure of the dosage form. Wall 12 can be applied around the slow releasing lamina and the fast releasing lamina by molding, spraying, or dipping the pressed laminae into the wall forming composition. Another and presently preferred technique that can be used for applying the wall is the air suspension procedure. This procedure consists in suspending and tumbling the pressed compositions in a current of air and a wall forming composition until the wall surrounds and coats the two pressed together laminae. The air suspension procedure is well suited for independently forming the wall The air suspension procedure is described in U.S. Pat. No. 2,799,241; in *J. Am. Pharm. Assoc.*, Vol. 48, pp 451–459 (1959) and *ibid*, Vol. 49, pp 82–84, (1960). A dosage forming system can be coated also with a wall forming composition with a Wurstere ® air suspension coater using organic solvents such a methylene dichloride/methanol cosolvent, 80/20 wt/wt, using 2.5% to 4% solids. The Aeromatic ® air suspension coater using a methylene dichloride/methanol cosolvent, 87/13 wt/wt, also can be used for applying the wall of the lamina. Other wall forming techniques such as pan coating can be used for applying the wall. In the pan coating system a wall forming composition is deposited by successive spraying of the compositions on the drug accompanied by tumbling the compressed fast and slow releasing laminate in a rotating pan. A pan coater is used, in one manufacture, to produce a thicker wall. A larger volume of methanol can be used in a cosolvent to produce a thinner wall. Finally, the wall or lamina coated laminae are dried in a forced air oven at 50° C. for one to seven days to free the dosage form of solvent. Generally, the wall formed by these techniques will have a thickness of 2 to 20 mils, with a presently preferred thickness of 4 to 10 mils.

Exemplary solvents suitable for manufacturing the lamina include inorganic and organic solvents that do not adversely harm the lamina, the lamina forming ingredients and the final dosage form. The solvents broadly include a member selected from the group consisting of alcohols, ketones, esters, ethers, aliphatic hydrocarbons, halogenated solvents, cycloaliphatic solvents, aromatic, heterocyclic solvents, and mixtures thereof. Typical solvents include acetone, diacetone, methanol, ethanol, isopropyl alcohol, butyl alcohol, methyl acetate, ethyl acetate, isopropyl acetate, n-butylacetate, methyl isobutyl ketone, methyl propyl ketone, n-hexane, n-heptane, methylene dichloride, ethylene dichloride, propylene dichloride, ethyl ether, mixtures such as acetone and ethanol, acetone and water, acetone and methanol, methylene dichloride and methanol, ethylene dichloride and methanol, and the like.

The following examples illustrate means and methods for carrying out the present invention. The examples are merely illustrative and they should not be considered as limiting the scope of the invention, as these examples and other equivalents thereof will be come more apparent to those versed in the pharmaceutical dispensing art in the light of the present disclosure, the drawings and the accompanying claims

EXAMPLE

A dosage form for the controlled delivery of the beneficial drug acetaminophen is made as follows: First, a slow acetaminophen releasing lamina is prepared by blending 19.375 g of acetaminophen, 1.625 g of hydroxypropylmethylcellulose having a molecular weight of 9,200, 2.875 g of lightly cross-linked sodium carboxymethylcellulose, and 1 g of polyvinylpyrrolidone in a V-blender for 20 to 25 minutes. Then, the homogeneous blend is transferred to a beaker and 10 ml of absolute ethanol is added to the blend and the mixing continued for an additional ten minutes The wet blend is passed through a number 20 mesh screen to produce wet granules. The granules are dried at room temperature for 16 hours, and then passed through a 20 mesh screen. Next, the granules are lubricated with 0.125 g of magnesium stearate in a V-blender for 3 minutes.

Next, a fast releasing acetaminophen lamina is made by intimately blending 18.125 g of acetaminophen, 6.25 g of hydroxypropylcellulose exhibiting a hydroxypropoxy content of 10% to 13%, and 0.5 g of polyvinylpyrrolidone are blended for 20 minutes and then transferred to a beaker Then, 10 ml of absolute alcohol is added to the blend and the blending continued for about 10 minutes. The wet blend then is passed through a 20 mesh screen and allowed to dry for 16 hours at room temperature. The dry blend is again screened through a 20 mesh screen. The dry granules are placed in a V-blender and blended with 0.125 g of magnesium stearate for 3 minutes.

Next, 451.6 mg of the slow drug releasing formulation is pressed into a 7/10″ oval shape on a Manesty ® layer press and 206.9 mg of the fast releasing drug layer is pressed on top of the slow releasing layer to provide a bilayer drug core.

Next, the bilamina is surrounded with a semipermeable wall. The semipermeable wall forming composition comprises 80% cellulose acetate having an acetyl content of 39.8%, 10% hydroxypropylmethylcellulose having a molecular weight of 11,300 (HPMC E-5), and 10% polyethylene glycol. The semipermeable wall is applied in an Aeromatic ® air suspension coater. A coating solution comprising the cellulose acetate, hydroxypropylmethylcellulose and the polyethylene glycol dissolved in methylene chloride-methanol, 90:10 wt %, to give 4% solids, is sprayed around the bilamina to provide the wall. Next, the semipenmeable wall coated dosage forms are dried in a forced air oven for 16 hours at 50° C. to evaporate the solvents.

Figure 3:
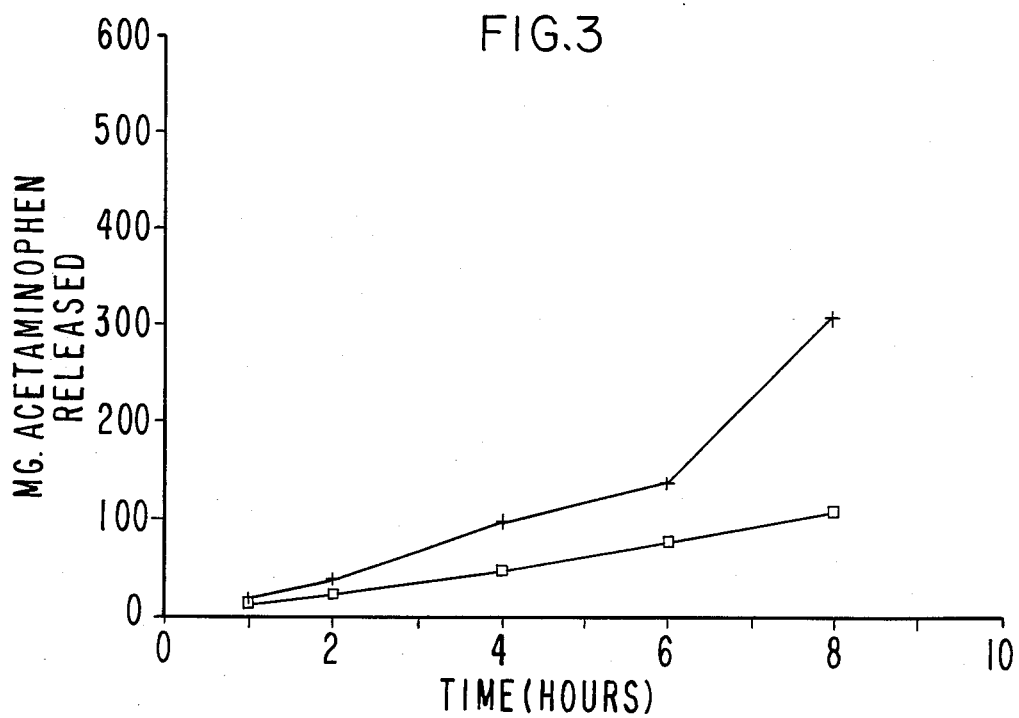
FIG. 3 is a graph depicting the amount of beneficial agent delivered in different agent receiving environments.
Figure 4:
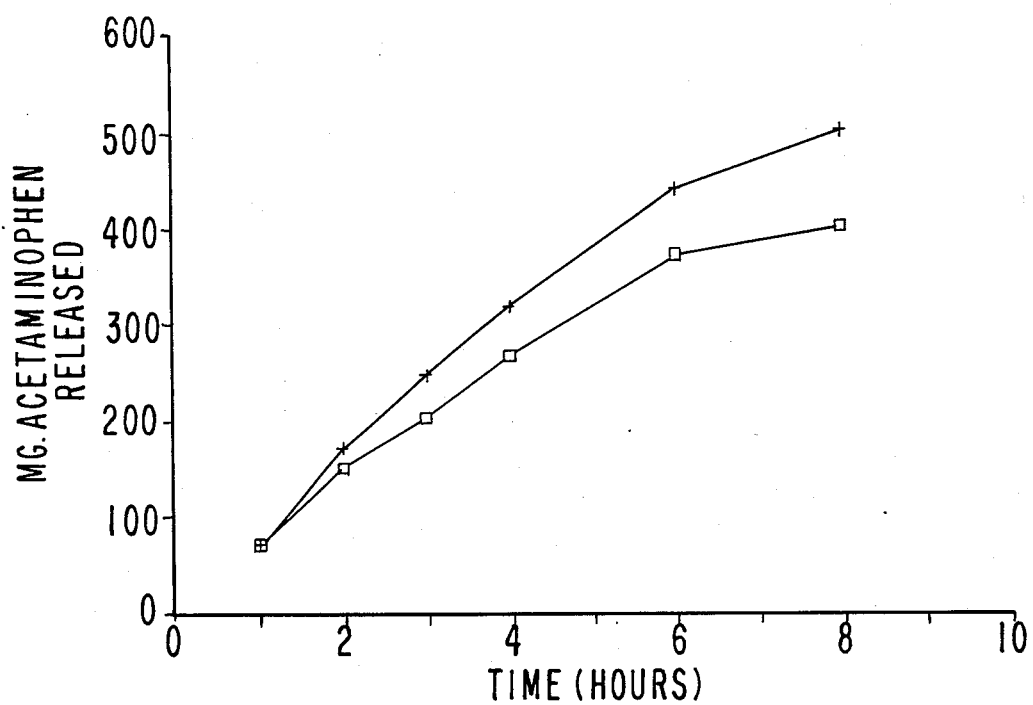
FIG. 4 is a graph depicting the amount of beneficial agent delivered in different agent receiving environments with the dosage form comprising different exit means.

Next, the dried dosage forms are divided into two groups. One group is drilled with a 50 mm orifice on two faces of the dosage form. The other group is drilled with a 20 mil wide by 197 mil long slit on each face. Then, both groups of dosage forms are placed in artificial gastric fluid and artificial intestinal fluid at 37° C. and the release rate ascertained in a USP release rate tester. The release rates for the dosage forms with the two orifices is seen in FIG. 3. In FIG. 3 dosage form 10 comprises two 50 mil passageways. The release rate curve with the connecting squares denotes measurements made in artificial intestinal fluid and the release rate curve connected with plus marks denotes measurement made in artificial gastric fluid. In FIG. 4, the dosage form comprises two 0.5 cm slits. In FIG. 4 the release rate curve with the connecting squares denotes measurements made in artificial intestinal fluid, and the release rate curve connected by plus signs denotes the release rate measured in artificial gastric fluid.

EXAMPLE 2

A dosage form for delivering a beneficial drug to an environment of use is prepared as follows: A slow drug releasing lamina is fluid bed granulated in a Vector Freund Flo-Coater. The slow drug releasing lamina is prepared as follows: First, 22.25 kg of acetaminophen and 6.0 kg of polyethylene oxide having a molecular weight of 200,000 are placed in the bowl of the fluid bed granulator. Then, while the powders are mixing, 30 kg of a solution of of 5% hydroxypropylmethylcellulose exhibiting a molecular weight of 11,300 in distilled water is sprayed onto the ingredients to form a granulation. Then, 150 g of magnesium stearate is added to the granulation in a Rotocone ® blender and mixing continued for 5 minutes. The granulation's final composition comprises 74.5% acetaminophen, 20% polyethylene oxide, 5% hydroxypropylmethylcellulose and 0.5% magnesium stearate.

Next, a fast drug releasing layer is prepared as follows. 23.25 kg of acetaminophen, 2.1 kg of hydroxypropylcellulose exhibiting a hydroxypropoxy content of 10% to 13%, 3 kg of sodium bicarbonate and 0.09 kg of ferric oxide are placed in a granulator bowl of a Vector-Freund Flocoater. While the ingredients are mixing in the granulator, 30 kg of a 5% hydroxypropylmethyl cellulose, having an average molecular weight of 11,300-E5, in water is sprayed onto the powders to form granules. The granules then are lubricated with 154.7 g of magnesium stearate for 5 minutes in a Rotocone blender. The final composition prepared by the granulation comprises 77.3% acetaminophen, 10% sodium bicarbonate, 7% hydroxypropylcellulose, 5% hydroxypropylmethylcellulose. 0.5% magnesium stearate and 0.3% ferric oxide.

The two lamina forming compositions were compressed into a bilaminate using a Manesty ® press. First, 469.8 mg of the slow formulation is added to the Manesty press and pressed to form a lamina. Then, 194.1 mg of the fast formulation is added to the Manesty press and pressed to form a fast releasing lamina in contact with the slow releasing lamina.

Next, the bilaminate is coated with a semipermeable wall. The semipermeable wall weighs 35.2 mg and comprises 70% cellulose acetae having an acetyl content of 39.8%, 15% polyethylene glycol 3350, and 15% hydroxypropylmethylcellulose having a number average molecular weight of 11,300. The semipermeable wall is applied in an AccelaCota ® rotating open coater. The coating solution consists of the cellulose acetate, the polyethylene glycol and the hydroxypropylmethylcellulose dissolved in methylene chloride:methanol, (90:10 wt%) to give a 4% solution.

After drying a slit passageway is formed in the wall using a laser generator. First a slit is laser drilled through the wall to connect the fast releasing lamina with the exterior of the dosage form. Then the dosage form is turned over and a laser slit passageway is drilled through the wall to the slow releasing lamina.

Figure 5:
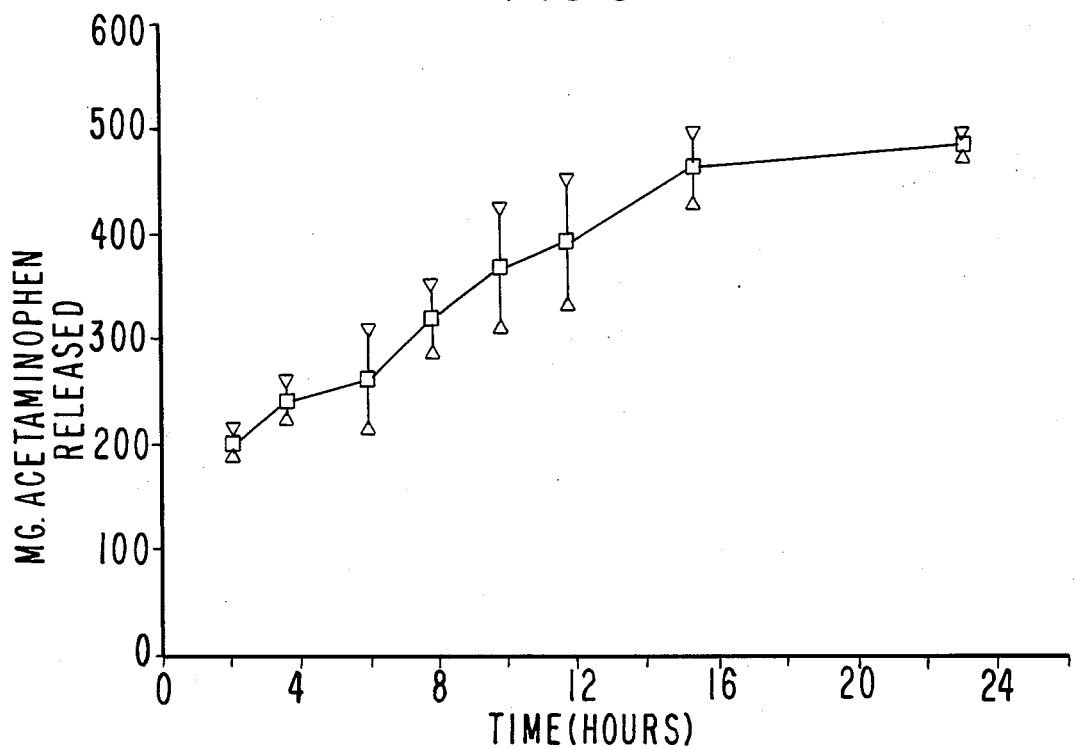
FIG. 5 is a graph depicting the total amount of beneficial agent delivered over a prolonged period of time.

The release of drug from the dosage form is measured in artificial gastric fluid. The cumulative release rate is depicted in FIG. 5.

EXAMPLE 3

Figure 6:
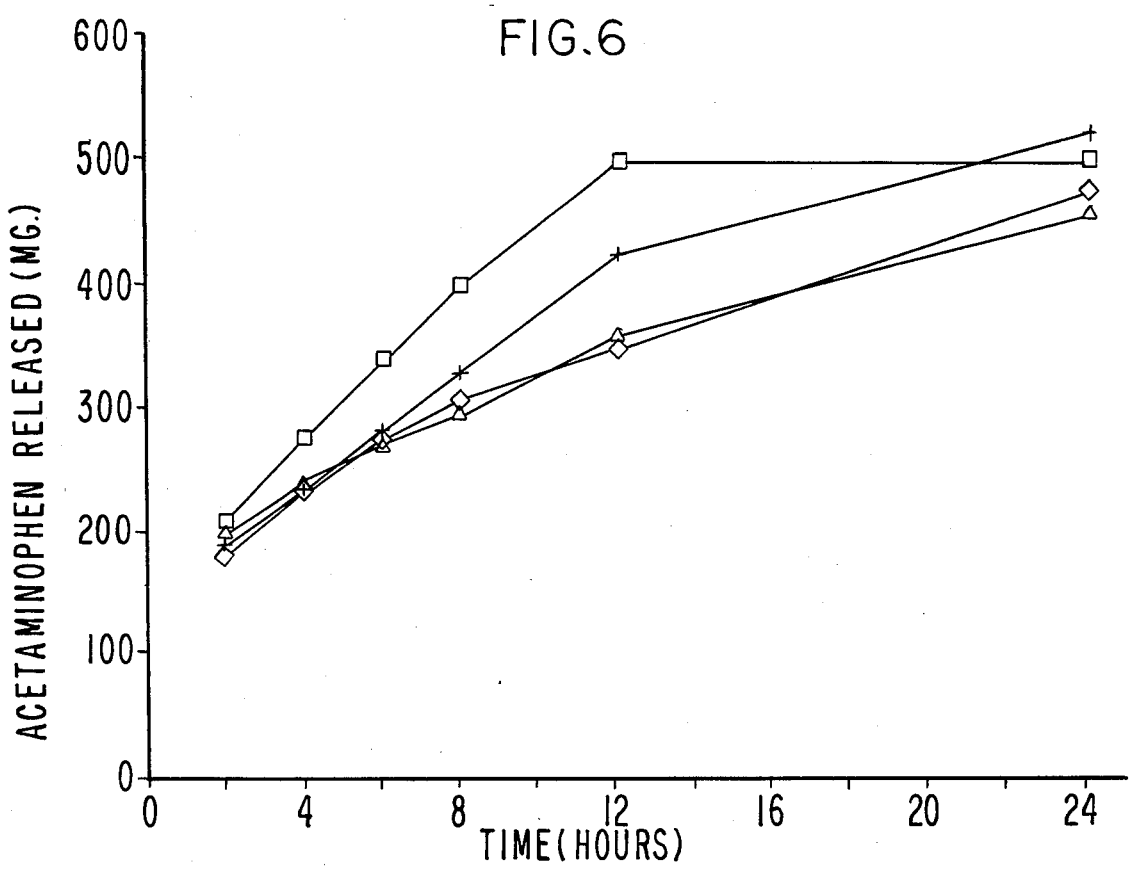
FIG. 6 is a graph depicting the amount of beneficial agent delivered through exit means of different dimensions; and, FIG. 7 is a graph depicting the effect of the weight of the wall on the amount of beneficial agent delivered from dosage forms; In the drawings and in the specification like parts in related figures are identified by like numbers. The terms appearing earlier in the specification and in the drawings, as well as embodiments thereof, are further described elsewhere in this specification.

The procedure of example 2 is followed in preparing this example. The dosage form prepared in this example comprises (1) a fast dissolving lamina comprising 77.5% acetaminophen, 10% sodium bicarbonate, 7% hydroxypropylcellulose, 5% hydroxypropylmethylcellulose having a molecular weight of 11,300, and 0.5% magnesium stearate, (2) a slow releasing lamina comprising 74.5% acetaminophen, 20% polyethylene oxide having a molecular weight of 200,000, 5% hydroxypropylmethylcellulose having a molecular weight of 11,300 and 0.5% magnesium stearate, and (3) a wall comprising 70% cellulose acetate having an acetyl content of 39.8%, 15% hydroxypropylmethylcellulose having a molecular weight of 11,300 and 15% polyethylene glycol 3350. In this example cumulative release rates are measured for dosage forms with different slit passageways are plotted in FIG. 6, the line connected through squares indicates the cumulative amount released for a dosage form comprising two slit passageways measuring 1.25 cm×0.0007 cm; the line connected by plus signs denotes a dosage form comprising two slits of 1.25 cm×0.03 cm; the line connected by diamonds indicates a dosage form with one slit 1 cm×0.07 cm, and the line connected through triangles denotes a dosage form with a single slit passageway 1.5 cm×0.04 cm. In one preferred embodiment the passageway exhibits an area of 0.20 to 0.40 cm$^2$.

EXAMPLE 4

Figure 7:
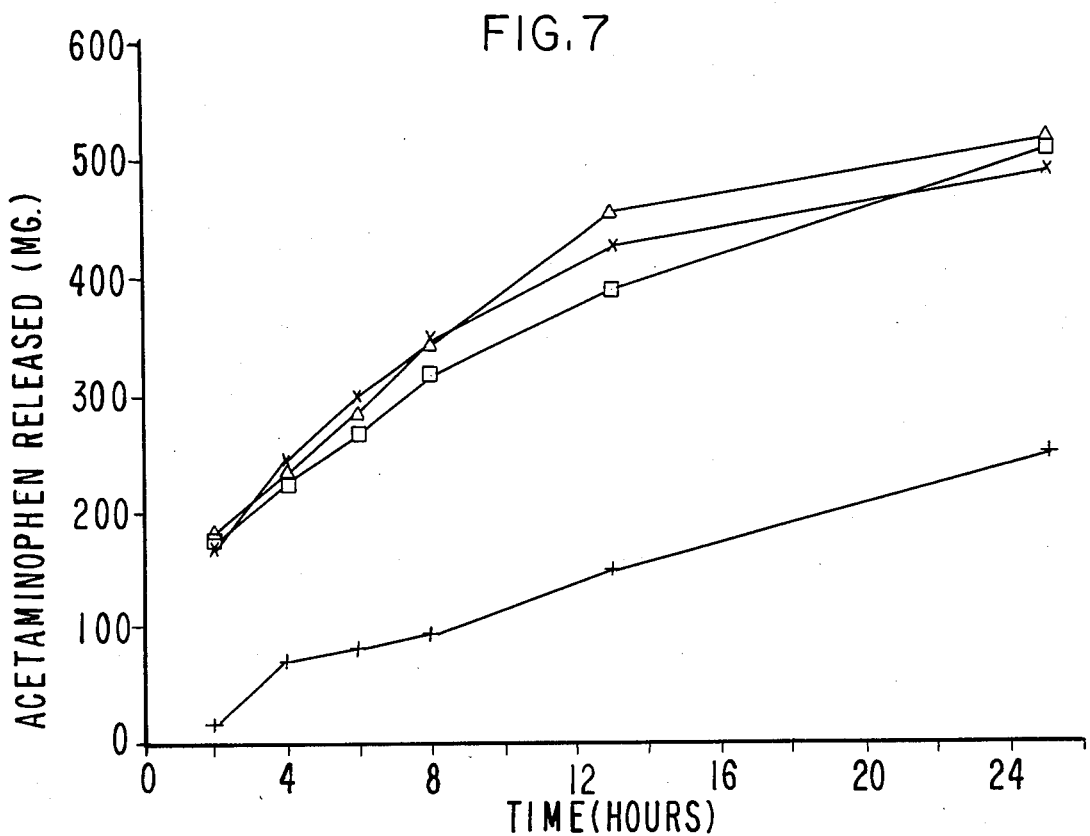

This example illustrates the effect of the weight of the wall on the cumulative amount released from a dosage form. In accompanying FIG. 7, the cumulative amount of acetaminophen released from a dosage form comprising a single passageway, a slow releasing lamina and a fast releasing lamina are illustrated as follows: the line connected with squares indicates the amount released from a dosage form with a wall weighing 13.1 mg, the lines connected by plus signs indicate the amount released when the wall weighs 77 mg, the line with triangles indicates the amount released when the wall weighs 25 mg, and line with X's indicates the cumulative amount released when the wall weighs 31 mg.

EXAMPLE 5

This example illustrates the release rate of dosage forms wherein the slow releasing lamina comprises different components. The fast releasing lamina of the dosage form comprises 80.0% phenylpropanolhydrochloride (PPA+Cl), 10% hydroxypropylcellulose, 5% sodium bicarbonate and 4.75% hydroxypropylmethylcellulose having a molecular weight of 11,300 and 0.25% magnesium stearate. The fast releasing lamina is used in two dosage forms comprising different slow releasing lamina. The slow releasing laminae are (a) a slow releasing lamina comprising 10% hydroxypropylmethylcellulose having a molecular weight of 9,200, 4% hydroxypropylmethylcellulose having a molecular weight of 241,900, 3% hydroxypropylcellulose, 2% hydroxypropylmethylcellulose having a molecular weight of 11,300, 80.5% PPAHCl and 0.5% magnesium stearate; and (b) a slow releasing lamina comprising 4% hydroxypropylmethylcellulose having a molecular weight of 241,900, 3% hydroxypropylcellulose, 12% hydroxypropylmethylcellulose having a molecular weight of 11,300, 80.5% PPAHCl and 0.5% of magnesium stearate. The slow releasing lamina weight is 62.11 mg and the fast releasing lamina weight if 31.25 mg. The fast and slow releasing bilaminate is surrounded by a wall with a slit passageway on each face. The fast releasing lamina releases 25 mg of PPAHCl in a short period and the slow releasing lamina releases 50 mg of PPAHCl over a prolonged period.

An embodiment of the invention pertains to administering a beneficial drug to an animal, such as a human. The method for administering a beneficial drug at a controlled rate comprises the steps of: (A) admitting into an animal a dosage form comprising (1) a wall comprising at least in part a semipermeable polymeric composition permeable to the passage of fluid and substantially impermeable to the passage of drug, the wall surrounding (2) an internal lumen; (3) a fast dissolving lamina in the lumen that is delivered form the dosage form in from 1 minute to 2 hours; (4) a slow releasing lamina in the lumen that is delivered from the dosage form in from 1½ hours to 24 hours; (5) a drug in the fast releasing lamina; (6) a drug in the slow releasing lamina, said drug the same or a different drug than in the fast releasing lamina; (7) exit means through the wall connecting the fast releasing lamina with the exterior of the dosage form, said exit means sized for delivering the fast releasing lamina from the dosage form in from 1 minute to 2 hours; (B) imbibing fluid through the semipermeable wall into each lamina at a rate determined by the permeability of the semipermeable wall and the osmotic pressure gradient across the wall to continuously change the lamina into a dispensable formulation; and, delivering the lamina under hydrostatic pressure from the dosage form to the animal for administering the drug to produce a therapeutic result.

The novel dosage form of this invention comprises means for the obtainment of precise release rate in the environment of use while simultaneously providing beneficial therapy to a recipient. Where there has been described and pointed out features of the invention as applied to presently peferred embodiments, those skilled in the dispensing art will appreciate that various modifications, changes, additions and omissions in the dosage form illustrated and described can be made without departing from the spirit of this invention.

We claim:
1. A method for administering a beneficial agent to an animal, said method comprising:
   (a) admitting into the animal dosage form comprising:
   (1) a wall comprising at least in part a semipermeable composition permeable to the passage of fluid and substantially impermeable to the passage of beneficial agent the wall surrounding:
   (2) a lumen;
   (3) a first lamina composition in the lumen, said first lamina composition means for forming a dispensable composition that is delivered from the dosage form in a short period of time;
   (4) a second lamina composition in the lumen, said second lamina composition comprising means for forming a dispensable composition that is delivered from the dosage form over a long period of time;
   (5) a beneficial agent in each lamina composition;
   (6) at least one exit means through the wall connecting the exterior of the dosage form with the lumen, said exit means sized for delivering the first dispensable composition in a short period of time;
   (b) imbibing fluid through the wall into each lamina composition at a rate determined by the permeability of the wall to provide fluid means for forming the dispensable composition; and
   (c) delivering the dispensable composition through the passageway from the dosage form to the animal for administering the beneficial agent to produce a beneficial result.

2. The method for administering the beneficial agent to an animal according to claim 1, wherein the dosage form comprises an exit means through the wall connecting the lamina that is delivered over a long period of time with the exterior of the dosage form.

3. The method for administering the beneficial agent to an animal according to claim 1, wherein the short period of time is from 1 minute to 2 hours.

4. The method for administering the beneficial agent to an animal according to claim 1, wherein the long period of time is from 1 to 1½ hours up to 24 hours.

5. The method for administering the beneficial agent to an animal according to claim 1, wherein the beneficial agent is a drug.

6. The method for administering the beneficial agent to an animal according to claim 1, wherein the animal is a human.

7. The method for administering the beneficial agent to an animal according to claim 1, wherein the dosage form is orally admitted into the animal.

8. The method for administering the beneficial agent to an animal according to claim 1, wherein the dispensable composition that is delivered in a short period of time is delivered first and the dispensable composition that is delivered over a long period of time is delivered thereafter.

9. A dosage form for delivering a beneficial agent to an environment of use, wherein the dosage form comprises:
   (a) a wall comprising at least in part a semipermeable composition permeable to the passage of fluid and substantially impermeable to the passage of beneficial agent, which wall surrounds and forms;
   (b) a compartment;
   (c) a first lamina composition in the compartment comprising means for delivering a beneficial agent from the dosage form in a short period of time;
   (d) a second lamina composition in the compartment comprising means for delivering a beneficial agent from the dosage form over a long period of time;
   (e) a beneficial agent selected from like and unlike beneficial agents in each lamina; and,
   (f) at least one exit means in the wall communicating the exterior of the dosage form with the compartment, said exit means shaped and sized for delivering said first dispensable composition in a short period of time, through the exit means to the environment of use.

10. The dosage form for delivering the beneficial agent to the environment of use according to claim 9, wherein the environment of use is a warm-blooded animal.

11. The dosage form for delivering the beneficial agent to the environment of use according to claim 9, wherein the environment of use is a human.

12. The dosage form for delivering the beneficial agent to the environment of use according to claim 9, wherein the environment of use is a gastrointestinal tract and the dosage form is orally admitted into the gastrointestinal tract.

13. The dosage form for delivering the beneficial agent to the environment of use according to claim 9, wherein the beneficial agent is a drug and the dosage form is a drug administration device.

14. The dosage form for delivering the beneficial agent to the environment of use according to claim 9, wherein the first lamina composition that is delivered in a short period of time comprises a gel composition, and the second lamina composition that is delivered in a long period time comprises a different gel composition.

15. The dosage form for delivering the beneficial agent to the environment of use according to claim 9, where the first lamina composition that is delivered in a short period of time comprises a cellulosic composition, and the second lamina composition that is delivered in a long period of time comprises a different cellulosic composition.

16. The dosage form for delivering the beneficial agent to the environment of use according to claim 9, wherein the exit means is longer than wide.

17. The dosage form for delivering the beneficial agent to the environment of use according to claim 9, wherein the first lamina composition that is delivered in a short period of time is initially in contact with the second lamina composition that is delivered in a long period of time.

18. The dosage form for delivering the beneficial agent to the environment of use according to claim 9, wherein the first lamina composition lamina that is delivered in a short period of time is parallel with the second lamina composition that is delivered in a long period of time.

19. The dosage form for delivering the beneficial agent to the environment of use according to claim 9, wherein the second lamina composition that is delivered in a long period of time is thicker than the first lamina composition that is delivered in a short period of time.

20. The dosage form for delivering the beneficial agent to the environment of use according to claim 9, wherein the second lamina composition that is delivered in a long period of time comprises at least one polymeric member exhibiting a larger molecular weight than a polymeric member in the first lamina composition that is delivered in a short period of time.

* * * * *